US006387258B1

(12) United States Patent
Keri et al.

(10) Patent No.: US 6,387,258 B1
(45) Date of Patent: May 14, 2002

(54) METHOD OF PURIFYING STATINS FROM A FERMENTATION BROTH

(75) Inventors: Vilmos Keri; Lajos Deak; Iiona Forgacs, all of Debrecen (HU)

(73) Assignee: Biogal Gyogyszergyar Rt., Debrecen (HU)

( * ) Notice: Subject to any disclaimer, the term of this patent is extended or adjusted under 35 U.S.C. 154(b) by 0 days.

(21) Appl. No.: 09/769,684

(22) Filed: Jan. 25, 2001

Related U.S. Application Data

(60) Provisional application No. 60/184,522, filed on Feb. 24, 2000.

(51) Int. Cl.$^7$ .................. B01J 15/08; B01D 15/08; C12D 7/00; C12D 17/06; C07D 311/04

(52) U.S. Cl. ............... 210/198.2; 210/656; 435/125; 435/129; 435/130; 435/132; 549/289; 549/292; 549/299; 560/129; 560/130

(58) Field of Search ............... 549/292, 289, 549/399; 560/129, 130; 435/125, 132; 210/198.2, 656

(56) References Cited

U.S. PATENT DOCUMENTS

| | | | |
|---|---|---|---|
| 3,983,140 A | 9/1976 | Endo et al. ............ 549/292 |
| 4,049,495 A | 9/1977 | Endo et al. ............ 514/548 |
| 4,294,846 A | 10/1981 | Albers-Schonberg et al. ............ 514/460 |
| 4,294,926 A | 10/1981 | Monaghan et al. ...... 435/125 |
| 4,319,039 A | 3/1982 | Albers-Schonberg ..... 435/125 |
| 4,342,767 A | 8/1982 | Albers-Schonberg et al. ............ 514/548 |
| 4,420,491 A | 12/1983 | Albers-Schonberg et al. ............ 424/311 |
| 5,202,029 A | 4/1993 | Haytko et al. |
| 5,403,728 A | 4/1995 | Jekkel et al. ............ 435/125 |
| 5,409,820 A | * 4/1995 | Gerson et al. ........... 435/125 |
| 5,616,595 A | 4/1997 | Chu et al. ............. 514/344 |
| 5,691,173 A | * 11/1997 | Primrose et al. ......... 435/125 |
| 5,712,130 A | * 1/1998 | Hajko et al. ............ 435/123 |
| 5,989,877 A | 11/1999 | DePater et al. |

FOREIGN PATENT DOCUMENTS

| | | | |
|---|---|---|---|
| CA | 2129416 | 8/1994 | ............ 435/125 |
| DE | 44 02 591 | 1/1994 | ............ 435/123 |
| GB | 2 046 737 | 2/1980 | ............ 435/125 |
| HU | 208 997 | 6/1992 | ............ 435/125 |
| WO | WO 00/63411 | * 10/2000 | ............ 549/292 |

OTHER PUBLICATIONS

Joel G. Hardman, et al, *The Pharmacological Basis of Therapeutics*, 9$^{th}$ edition, 1996, p. 879.

Andrew Streitweiser, Jr., et al., *Introduction to Organic Chemistry*, MacMillan Publishing Co., 2$^{nd}$ ed., 1981, pp. 858–860.

* cited by examiner

*Primary Examiner*—Alan L. Rotman
*Assistant Examiner*—Raymond Covington
(74) *Attorney, Agent, or Firm*—Kenyon & Kenyon

(57) ABSTRACT

A process for purifying statin compounds from a fermentation broth by extraction and crystallization is disclosed. A fermentation broth is subjected to a pretreatment procedure which involves an alkaline pretreatment and an alkaline purification. Following the pretreatment procedure, the statin compound is extracted under acidic conditions into a hydrophobic solvent and purified by crystallization. The organic extraction solvent is concentrated and then extracted with a mild base. The statin compound is then purified by crystallization.

29 Claims, No Drawings

METHOD OF PURIFYING STATINS FROM A FERMENTATION BROTH

CROSS-REFERENCE TO RELATED APPLICATION

This application claims the benefit of the provisional application Serial No. 60/184,522, filed Feb. 24, 2000, the contents of which are incorporated herein by reference.

FIELD OF THE INVENTION

The present invention relates to methods for purifying compounds from a fermentation broth. More specifically, this invention relates to isolation of statins from a fermentation broth in a crystalline form.

BACKGROUND OF THE INVENTION

Complications of cardiovascular disease, such as myocardial infarction, stroke, and peripheral vascular disease account for half of the deaths in the United States. A high level of low density lipoprotein (LDL) in the bloodstream has been linked to the formation of coronary lesions which obstruct the flow of blood and can rupture and promote thrombosis. Goodman and Gilman's, *The Pharmacological Basis of Therapertics* 879 (Joel G. Hardman et al., eds. 9th ed. 1996). Reducing plasma LDL levels has been shown to reduce the risk of clinical events in patients with cardiovascular disease and in patients who are free of cardiovascular disease but who have hypercholesterolemia. Scandinavian Simvastatin Survival Study Group, 1994; Lipid Research Clinics Program, 1984a, 1984b.

Statin drugs are currently the most therapeutically effective drugs available for reducing the level of LDL in the blood stream of a patient at risk for cardiovascular disease. This class of drugs includes, inter alia, compactin, lovastatin, simvastatin, pravastatin and fluvastatin. The mechanism of action of statin drugs has been elucidated in some detail. They disrupt the synthesis of cholesterol and other sterols in the liver by competitively inhibiting the 3-hydroxy-3-methylglutaryl-coenzyme A reductase enzyme ("HMG-CoA reductase"). HMG-CoA reductase catalyzes the conversion of HMG-CoA to mevalonate, which is the rate limiting step in the biosynthesis of cholesterol. Consequently, its inhibition leads to a reduction in the rate of formation of cholesterol in the liver.

Compactin is the common medicinal name of the chemical compound 2-methylbutanoic acid 1,2,3,7,8,8a-hexahydro-7-methyl-8-[2-(tetrahydro-4-hydroxy-6-oxo-2H-pyran-2-yl)ethyl]-1-naphthalenyl ester of the formula:

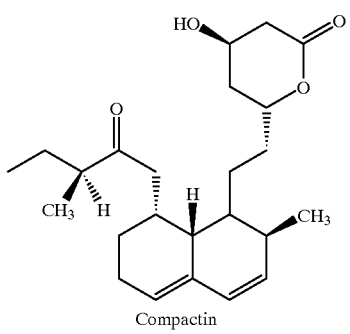

Compactin

Compactin, also called mevastatin, was the first statin drug shown to be a HMG-CoA reductase inhibitor. Compactin has been purified from *Penicillium citrinum* and *Penicillium adametzioides*. (See U.S. Pat. Nos.3,983,140; 4,049,495 and; 5,691,173 which are incorporated herein by reference.)

Lovastatin is the common medicinal name of the chemical compound 2-methylbutanoic acid 1,2,3,7,8,8a-hexahydro-3,7-dimethyl-8-[2-(tetrahydro4-hydroxy-6-oxo-2H-pyran-2-yl)ethyl]-1-naphthalenyl ester of the formula:

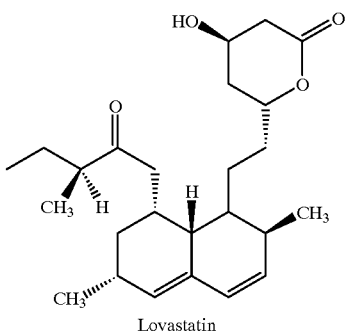

Lovastatin

Lovastatin, also called mevinolin, differs from compactin only in the presence of a methyl group and can be isolated from *Aspergillus terreus*. (See U.S. Pat. Nos. 4,294,926; 4,420,491; 4,319,039; and 4,294,896 which are incorporated herein by reference.) Lovastatin has also been isolated from several other microorganisms. (See British Patent No. GB 2,046,737; German Patent No. 44 02 591; Canadian Patent No. 2,129,416; and Hungarian Patent No. HU 208,997.)

Compactin and lovastatin, as well as other statins, exist as open ring hydroxy-acids and in the lactone form as shown:

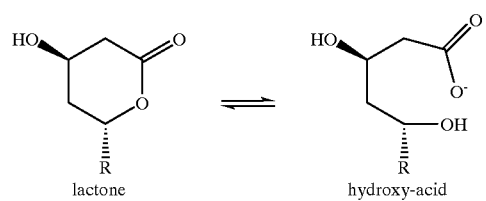

The equilibrium between lactone and hydroxy-acid makes purification difficult because the free acid and the lactone forms of the statin compounds have different polarities. A method of purifying one form is likely to remove the other form, thereby decreasing overall yield. Consequently, great care must ordinarily be exercised when purifying statin compounds in order to isolate them in high yield.

U.S. Pat. No. 5,202,029 relates to a process for purifying the lactone form of statin compounds using HPLC. The crude fermentation broth (e.g., lovastatin, simvastatin, pravastatin, fluvastatin and mevastatin) is dissolved in an organic solvent and eluted through a HPLC column. The statin elutes from the column as a solute dissolved in the eluant. The eluant is partially evaporated and subsequently water is added to induce crystallization. The primary disadvantage for industrial scale production is the great expense of the chromatography columns.

U.S. Pat. No. 5,616,595 relates to a continuous process for recovering a wide variety of water-insoluble compounds from a fermentation broth by tangential filtration. The process may be applied to the lactone form of lovastatin, pravastatin and simvastatin. The process comprises cycling a fermentation broth through a filter which retains the insoluble compound. The compound is dissolved in a solvent and the solution filtered. The solution of the desired compound is collected as the filtrate and the desired compound may then be subjected to further purification. Because of the insolubility of the compounds in water, the process requires solvent for solubilization and multiple filtration membranes are required. The repeated filtration renders the process very costly for large scale manufacture.

A process for isolating lovastatin in the lactone form is described in U.S. Pat. No. 5,712,130. In this process, lovastatin is extracted from a fermentation broth with butyl acetate. The resulting solution is then centrifuged and an aqueous phase is discarded. The organic phase is, vacuum distilled at above 40° C., which, in addition to concentrating the solution, promotes formation of the lactone by removal of water. Crystals of lovastatin lactone form upon cooling and are recrystallized to a purity of 90% or greater. However, prior to use as a pharmaceutical the crystalized lovastatin must be further purified, which decreases the overall yield and adds additional expenses to the procedure.

OBJECTS AND SUMMARY OF THE INVENTION

The known methods of isolating a statin from a fermentation broth do not achieve a pharmaceutically acceptable level of purity with a process economical on an industrial scale, or require chromatographic separation to achieve high purity. An object of the present invention is to meet a need in the art for a simple, fast, high yield process for isolation of statins from a fermentation broth at a pharmaceutically acceptable level of purity (i.e., not less than 98.5%).

Another object of the present invention is a process for isolating a statin compound from a fermentation broth, wherein the statin compound comprises a carboxylic acid capable of forming a lactone and a fused bicyclic ring. The process comprises the steps of: extracting the statin compound from the fermentation broth by contacting the fermentation broth with an extraction solvent, and extracting the statin compound from the fermentation broth into the extraction solvent, wherein the extraction solvent is a hydrophobic organic extraction solvent; separating the hydrophobic organic organic extraction solvent from the fermentation broth; concentrating a solution of the hydrophobic organic extraction solvent containing the extracted statin compound; and purifying the extracted statin compound by crystallization.

Another object of the present invention is a process for isolating a statin compound from a fermentation broth, wherein the statin compound comprises a carboxylic acid capable of forming a lactone and a fused bicyclic ring, the process comprising the steps of:

(a) pretreating the fermentation broth under alkaline conditions to remove non-polar impurities;

(b) extracting the statin compound from the fermentation broth into a hydrophobic organic extraction solvent;

(c) separating the hydrophobic organic extraction solvent from the fermentation broth;

(d) concentrating a solution of the hydrophobic organic extraction solvent containing the extracted statin compound;

(e) washing the concentrated solution of the hydrophobic organic extraction solvent with an aqueous solution containing a base to purify the lactone; and (g) purifying the extracted statin compound by crystallization.

DETAILED DESCRIPTION OF THE INVENTION

The present invention is a process for obtaining highly purified crystals of statin compounds from a fermentation broth, as illustrated by the purification of compactin and lovastatin. One of ordinary skill in the art will recognize that the process of the present invention may be used to purify other compounds that are made by a microbial or enzymatic process, and that contain a lactone such as simvastatin, pravastatin and fluvastatin. One of ordinary skill in the art will also recognize that optimal conditions for purifying a statin compound may vary depending upon the particular statin compound to be isolated, the fermentation broth and the microorganism producing the compound.

A preferred embodiment of the present invention involves the steps of: (i) pretreating the fermentation broth under alkaline conditions to remove non-polar impurities; (ii) extracting the statin under acidic conditions as a hydroxy acid or a lactone from the fermentation broth into a hydrophobic organic extraction solvent; (iii) separating the hydrophobic organic extraction solvent from the fermentation broth; (iv) concentrating the hydrophobic organic extraction solvent containing the extracted statin compound while forming the lactone; and (v) purifying the extracted statin compound by crystallization.

In an alternative embodiment of the invention, the step of pretreatment of fermentation broth under alkaline conditions is omitted.

In the alternative embodiment, prior to the crystallization, the concentrated hydrophobic organic solvent is washed with an aqueous solution containing a base to increase yields. The preferred basic solutions contain ammonium hydroxide ($NH_4OH$, pH of about 7.5 to about 10), or about 1–5% (w/w) sodium bicarbonate ($NaHCO_3$) or sodium carbonate ($Na_2CO_3$).

Pretreatment of the Fermentation Broth Under Alkaline Conditions

The pretreatment of the fermentation broth involves treatment of the fermentation broth under alkaline conditions followed by an extraction into a hydrophobic organic extraction solvent or solvent mixture. The alkaline conditions of the pretreatment step hydrolyze the lactone of the statin to the corresponding statin hydroxy acid. (Andrew Streitweiser, Jr. and Clayton Heathcock, *Introduction to Organic Chemistry*, 858–60 MacMillan Publishing Co., 2d Ed. 1981). The statin hydroxy acid is retained in the aqueous fermentation broth, while fatty and oily substances as well as other non-polar organic impurities from the fermentation broth partition into the pretreatment hydrophobic organic extraction solvent or solvent mixture. Thus, the pretreatment of the fermentation broth under alkaline conditions results in an overall purification of the statin hydroxy acid by separating the statin hydroxy acid from impurities.

Removal of non-polar impurities improves the overall yield of crystallization as it is believed that the presence of non-polar impurities within the fermentation broth reduces the overall yield of crystallization. Accordingly, the pretreatment of the fermentation broth under alkaline condition removes non-polar impurities from the fermentation broth, thereby significantly increases the overall yield of the crystallization step.

During the pretreatment step, the pH of the fermentation broth, or a mixture of the fermentation broth and hydrophobic organic extraction solvent, is adjusted to alkaline pH. Preferably the pH is adjusted by the addition of an inorganic base or an organic amine. Preferred inorganic bases or organic amines include NaOH, KOH, LiOH, $Ca(OH)_2$, $NH_4OH$ and triethylamine. Most preferably the base is NaOH. The pH is between about 7.0 and about 13.9. Preferably for compactin and lovastatin, the pH is adjusted in the range of about 8.5 and to about 10.0. Most preferably for compactin and lovastatin, the pH is about 9.0–about 9.6.

The pretreatment incubation under the alkaline conditions may be performed at temperatures of about 15° C. to about 100° C. Temperatures of about 15–20° C. result in decreased overall yield of purified statin.

At about 80° C. to about 100° C., the preferred conditions for pretreatment incubation are about 15 minutes at pH about 12.0 to about 13.9. At about 55 to about 65° C., the preferred conditions for pretreatment incubation are 2 hours at pH about 9.0 to about 9.6. At about 15 to about 25° C., the preferred conditions for pretreatment incubation are 48 hours at pH about 9.0 to about 9.6.

Pretreatment hydrophobic organic extraction solvents include but are not limited to i-butyl-acetate, n-butyl acetate, t-butyl acetate, ethyl acetate, propyl acetate, ethyl formate, butyl methyl ketone, dichloromethane, chloroform, carbon tetrachloride, dichloroethane, toluene, acetonitrile, methyl formate, methanol, ethanol, i-propanol, n-propanol, n-butanol, i-butanol, t-butanol, amyl alcohol and benzyl alcohol.

Alternatively, the pretreatment hydrophobic organic extraction solvent may comprise a mixture of any of the above solvents. Organic solvents for alkaline extraction include but not limited to i-butyl-acetate, n-butyl acetate, t-butyl acetate, ethyl acetate, propyl acetate, ethyl formate, butyl methyl ketone, dichloromethane, chloroform, carbon tetrachloride, dichloroethane, toluene, and benzyl alcohol. Preferred pretreatment hydrophobic organic extraction solvents are i-butyl acetate, ethyl acetate and toluene. The most preferred hydrophobic organic extraction solvent is i-butyl acetate. Alcohols work but are not preferred because of the solvent regeneration. Nevertheless, alcohols are present in the case of acetates at alkaline pH. The alcohols help the opening of the lactone ring at alkaline conditions. Pretreatment can also be carried out without extraction solvents.

In this preferred embodiment, after the pretreatment, the hydrophobic organic extraction solvent is contacted with the fermentation broth under alkaline conditions until fatty and oily substances as well as other non-polar organic impurities have been substantially depleted from the fermentation broth. Thin layer chromatography or any other method, including subjective judgment, may be used to assess depletion of non-polar polar impurities from the fermentation broth. Multiple extractions may be performed for optimal removal of impurities. However, one to two extractions is highly efficient when i-butyl acetate is used for alkaline extraction. Preferably, the alkaline extraction is conducted with a volume of solvent that is between about 20% to about 50% (v/v) the volume of the fermentation.

pH Adjustment Prior to the Extraction of Fermentation Broth under Acidic Conditions Preferably the pH of the purified fermentation broth is adjusted to between about 1.0 and about 6.4 with a strong acid prior to extraction of the statin compound into a hydrophobic organic extraction solvent. The preferred pH range for both Lovastatin and Compactin is between about 2.0 and about 4.5. The preferred pH range for Pravastatin is between about 4.5 and about 6.0. The preferred acids for pH adjustment are sulfuric acid and phosphoric acid. Alternatively, the extraction of the statin compound may be performed by adjusting the pH of the hydrophobic extraction solvent to a range of about 1.0 to about 6.4.

Extraction of Statin Compound under Acidic Conditions as a Hydroxy Acid or a Lactone The hydrophobic organic extraction solvent is contacted with the purified fermentation broth under acidic conditions until the hydroxy acid and the lactone have been substantially depleted from the fermentation broth. Thin layer chromatography or any other method, including the subjective judgment, may be used to assess recovery of the lactone into the hydrophobic organic extraction solvent. Multiple extractions may be performed for optimal recovery. However, two to three extractions are highly efficient when the hydrophobic organic extraction solvent is i-butyl acetate and the pH is in the optimal range as disclosed above. Preferably, the extraction is conducted with a volume of fermentation broth that is about twice the volume of the organic extraction solvent.

The most preferred hydrophobic organic extraction solvent for extracting compactin is i-butyl acetate. Other suitable hydrophobic organic extraction solvents include but are not limited to n-butyl acetate, t-butyl acetate, ethyl acetate, propyl acetate, ethyl formate, butyl methyl ketone, dichloromethane, chloroform, carbon tetrachloride, dichloroethane, and toluene. Preferred extraction solvents are i-butyl acetate, n-butyl acetate, ethyl acetate and butyl methyl ketone. At the acidic extraction, solvent mixtures are not used.

Phase Separation of the Fermentation Broth and the Hydrophobic Organic Extraction Solvent The fermentation broth may be separated from the hydrophobic organic extraction solvent by methods well known in the art. Preferred methods for separation include counter current extraction. Decanters are the known equipment for it. Following phase separation, the purity of the solvent may be improved by washing with water.

Concentrating the Hydrophobic Organic Extraction Solvent

The volume of the hydrophobic organic extraction solvent is reduced following phase separation. Volume reduction may be accomplished by evaporation under reduced pressure at a temperature between about 30 to about 90° C. Preferably, evaporation is performed at reduced pressure and a temperature between about 40 to about 70° C. Alternatively, evaporation of hydrophobic solvent is performed at an elevated temperature (below about 90° C.) under reduced pressure or at atmospheric pressure.

Purifying the Extracted Statin Compound by Crystallization

The hydrophobic organic extraction solvent is evaporated until the concentration of the statin compound to be crystallized is 50 to 250 g/l. Lovastatin is optimally crystallized at a concentration of 80 to 100 g/l; compactin is optimally crystalized at a concentration of 130 to 170 g/l; and, pravastatin is optimally crystallized at a concentration of 80 to 120 g/l.

Crystallization can be performed at ambient temperature overnight. The preferred temperature range is about −10 to about 5° C. Crystallization is most preferredly performed at about −10° C. for about 20 hours.

Crystallization may be performed in any of the following solvents, or combinations of the following solvents: ethanol, i-propanol, n-propanol, i-butanol, n-butanol, t-butanol, ethyl acetate, acetone, methanol, acetonitrile, ethyl formate, i-butyl acetate, t-butyl acetate, n-butyl acetate, toluene, propyl acetate and butyl methyl ketone. Preferred solvents include toluene, isopropanol, i-butyl acetate or a mixture of ethanol-water mixture. The most preferred solvents are i-butyl acetate and ethanol-water mixture.

The crystals obtained using the process of the preferred embodiment contain less than 3.6% (w/w) impurities and are obtained in greater than 75% w/w yield. For the statin purification obtained by recrystallization from water:ethanol, the preferred ratio of water to ethanol is about 0.8 to about 2.0. The most preferred ratio of water to ethanol is 0.9 to 1.2. The crystals obtained using the preferred embodiment are at least 98.5% (w/w) pure.

The present invention will be further explained in the following examples. Unless otherwise specified, all yields are listed in % (w/w) and represent the overall yields or yields of all steps. However, the present invention should not be construed as limited thereby. One of ordinary skill in the art will understand how to vary the exemplified preparations to obtain the desired results.

EXAMPLES

Example 1

Isolation of Compactin

A fermentation broth (70 m$^3$) containing 350 kg compactin was prepared by methods well known in the art. (See, e.g., U.S. Pat. Nos. 3,983,140; 4,049,495 and 5,691,173). i-Butyl acetate (35 m$^3$) and water (35 m$^3$) were added to the aqueous fermentation broth (70 m$^3$) in a continuous way. The pH was adjusted to about 9.0–9.6 by addition of concentrated NaOH. The mixture was then heated to 60° C. and maintained at that temperature for 2 hours. The resulting organic and aqueous phases were then separated using counter current separation. Sodium lauryl sulfate was added to help de-emulsify the mixture during the separation.

The purified fermentation broth was acidified to a pH of about 2.0–4.5 with sulfuric acid. i-Butyl acetate (35 m$^3$) was then added continuously and after mixing in situ, the i-butyl acetate phase containing compactin was separated continuously.

The i-butyl acetate phase was concentrated under vacuum to a volume of about 2,150 L. The concentrated solution was allowed to stand at 0–5° C. overnight, whereupon compactin crystalized in 78% (w/w) yield and 93% (w/w) purity. The crude compactin was then recrystallized from a 1.2:0.9 ethanol:water mixture in 75% (w/w) yield and 99.0% (w/w) purity.

Example 2

Isolation of Compactin without the Pre-Purification Step of Fermentation Broth Under Alkaline Conditions A fermentation broth containing compactin was prepared as in Example 1. The fermentation broth (50 L) was acidified to a pH of about 2.0–4.5 with sulfuric acid. i-Butyl acetate (25 L) and water (25 L) were then added and after mixing for about 0.5 hour, the i-butyl acetate phase containing compactin was separated. The extraction was repeated with pure i-butyl acetate (25 L). The combined i-butyl acetate phase was concentrated under vacuum to a volume of about 1.5 L. The concentrated solution was allowed to stand at 0–5° C. overnight, whereupon compactin crystalized in 33% (w/w) yield and 94.5% (w/w) purity. While Example 1 exemplifies the use of alkaline extraction, Example 2 differs in that it illustrates the use of the technologies without the alkaline extraction.

Example 3

Isolation of Compactin Pre-Treatment of Fermentation Broth Under Alkaline Conditions of Concentrated i-Butyl Acetate and Washing with NaHCO$_3$ A fermentation broth was prepared as in Example 1. i-Butyl acetate (25 L) and water (25 L) were added to an aqueous fermentation broth (50 L). The pH was adjusted to about 9.0–about 9.6 by addition of concentrated NaOH. The mixture was then heated to about 60° C. and maintained at that temperature for about 2 hours. The phases were then separated. Dodecyl trimethyl ammonium chloride was added to help de-emulsify the mixture during the separation. The purified fermentation broth was acidified to a pH of about 2.0–4.5 with sulfuric acid. i-Butyl acetate (25 L) was then added and after mixing for about 0.5 hour, the i-butyl acetate phase containing compactin was separated. The acid extraction was repeated with pure i-butyl acetate (25 L).

The combined i-butyl acetate phase was concentrated under vacuum to a volume of about 1.5 L. The concentrated solution was diluted to a volume of about 8 L and washed with saturated sodium bicarbonate. The washed solution was concentrated again to 1.5 L and it was allowed to stand at 0–5° C. overnight, whereupon compactin crystalized in 76.5% (w/w) yield and 98.9% (w/w) purity.

In the absence of a preliminary alkaline extraction, compactin was obtained in only 39% (w/w) yield and 99.1% (w/w) purity.

Example 4

Isolation of Compactin the Effect of Reduced Temperature During the Pretreatment of Fermentation Broth Under Alkaline Conditions A fermentation broth was prepared as in Example 1. i-Butyl acetate (25 L) and water (25 L) were added to an aqueous fermentation broth (50 L). The pH was adjusted to about 9.0–about 9.6 by addition of concentrated NaOH. The mixture was maintained at temperatures about 15–about 20° C. for about 2 hours. The phases were then separated. Dodecyl trimethyl ammonium chloride was then added to help de-emulsify the mixture during the separation. The purified fermentation broth was acidified to a pH of about 2.0–4.5 with sulfuric acid. i-Butyl acetate (25 L) was then added and after mixing for about 0.5 hour, the i-butyl acetate phase containing compactin was separated. The extraction was repeated with pure i-butyl acetate (25 L). The combined i-butyl acetate phase was concentrated under vacuum to a volume of about 1.5 L. The concentrated solution was allowed to stand at 0–5° C. overnight, whereupon compactin was crystalized. The crude compactin was then recrystallized from a 1.2:0.9 ethanol:water mixture. Overall yield was 67% (w/w) yield and 99.1% (w/w) purity.

Example 5

Isolation of Compactin: the Effect of Acidic pH of 1.0–2.0 at the Acidic Extraction and Reduced Temperature During Crystallization A fermentation broth was prepared as in Example 1. i-Butyl acetate (25 L) and water (25 L) were added to an aqueous fermentation broth (50 L). The pH was adjusted to about 9.0–about 9.6 by addition of concentrated NaOH. The mixture was maintained at about 60° C. for 2 hours. The phases were then separated. Dodecyl trimethyl ammonium chloride was then added to help de-emulsify the mixture during the separation. The fermentation broth was acidified to a pH of about 1.0–2.0 with sulfuric acid. i-Butyl acetate (25 L) was then added and after mixing for 0.5 hour, the i-butyl acetate phase containing compactin was separated. The extraction was repeated with pure i-butyl acetate (25 L).

The combined i-butyl acetate phase was concentrated under vacuum until the concentration of compactin was approximately 150 g/l. The concentrated solution was maintained at a temperature of about −10° C. for about 20 hours.

Crystals were filtered and washed with i-butyl acetate. The crude compactin was then recrystallized from a 1.2:0.9 ethanol:water mixture. Compactin was obtained in 67% yield (w/w) and 98.8% (w/w) purity. The acidic extraction (at pH of 1.0–2.0) reduced the yield.

When the procedure of this example with the pretreatment of fermentation broth under alkaline conditions step was performed at about 15° C., the overall yield of compactin was reduced to 60% (w/w) and 98.7% (w/w) purity.

Example 6

Isolation of Lovastatin

A fermentation broth containing lovastatin was prepared by methods well known in the art. (See U.S. Pat. Nos. 5,403,728; 4,420,491; 4,342,767; 4,319,039 and 4,294,846.) i-Butyl acetate (25 L) and water (25 L) were added to the aqueous fermentation broth (50 L). The pH was adjusted to about 9.0–about 9.6 by addition of concentrated NaOH. The mixture was then heated to about 60±5° C. and maintained at that temperature for about 2 hours. The phases were then separated. Dodecyl trimethyl ammonium chloride was added to help de-emulsify the mixture during the separation.

The purified fermentation broth was acidified to a pH of about 2.0–4.5 with sulfuric acid. i-Butyl acetate (25 L) was then added and after mixing for 2 hours, the i-butyl acetate phase containing lovastatin was separated. The extraction was repeated with pure i-butyl acetate (25 L).

The combined i-butyl acetate phase was concentrated under vacuum to a volume of about 2.7 L. The concentrated solution was allowed to stand at −10° C. for 36 hours, whereupon lovastatin crystalized in 76% (w/w) yield and 96.4% (w/w) purity. The crude lovastatin was then recrystallized from a 1.2:0.9 ethanol:water mixture in 71.4% (w/w) yield and 98.7% (w/w) purity.

Example 7

Isolation of Lovastatin without the Pre-Purification of Fermentation Broth Under Alkaline Conditions A fermentation broth containing lovastatin was prepared as in Example 6. The fermentation broth (50 L) was acidified to a pH of about 2.0–4.5 with sulfuric acid. i-Butyl acetate (25 L) and water (25 L) were then added and after mixing for about 2 hours, the i-butyl acetate phase containing compactin was separated. The extraction was repeated with pure i-butyl acetate (25 L). The combined i-butyl acetate phase was concentrated under vacuum to a volume of about 2.7 L. The concentrated solution was allowed to stand at −10° C. for 36 hours, whereupon lovastatin crystalized in 26% (w/w) yield and 88.0% (w/w) purity.

Example 8

Isolation of Lovastatin: Applying Washing with $NaHCO_3$

A fermentation broth was prepared as in Example 6. i-Butyl acetate (25 L) and water (25 L) were added to an aqueous fermentation broth (50 L). The pH was adjusted to about 9.0–about 9.6 by addition of concentrated NaOH. The mixture was then heated to about 60° C. and maintained at that temperature for about 2 hours. The phases were then separated. Dodecyl trimethyl ammonium chloride was added to help de-emulsify the mixture during separation. The purified fermentation broth was acidified to a pH of about 2.0–4.5 with sulfuric acid. i-Butyl acetate (25 L) was then added and after mixing for 2 hours, the i-butyl acetate phase containing compactin was separated. The extraction was repeated with pure i-butyl acetate (25 L).

The i-butyl acetate phase was concentrated under vacuum to a volume of about 2.7 L. The concentrated solution was diluted to a volume of about 11 L and it was washed with saturated sodium bicarbonate. The washed solution was concentrated again to 2.7 L and it was allowed to stand at −10° C. for 36 hours, whereupon lovastatin was obtained in 73.4% (w/w) yield and 98.8% (w/w) purity.

What is claimed is:

1. A process for isolating a statin compound from a fermentation broth, wherein the statin compound comprises a carboxylic acid capable of forming a lactone and a fused bicyclic ring, comprising the steps of:

(a) pretreating the fermentation broth under alkaline conditions to remove non-polar impurities;

(b) extracting the statin compound from the fermentation broth by contacting the fermentation broth with an extraction solvent, and extracting the compound from the fermentation broth into the extraction solvent, wherein the extraction solvent is a hydrophobic organic extraction solvent;

(c) separating the hydrophobic organic extraction solvent from the fermentation broth;

(d) concentrating a solution of the hydrophobic organic extraction solvent containing the extracted statin compound; and (e) purifying the extracted statin compound by crystallization.

2. The process of claim 1, wherein the statin compound is an inhibitor of HMG-CoA reductase.

3. The process of claim 1, wherein the statin compound is selected from the group consisting of lovastatin, compactin and pravastatin.

4. The process of claim 1, further comprising the step of pretreating the fermentation broth containing the statin compound under alkaline conditions.

5. The process of claim 4, wherein during the step of pretreating the fermentation broth, the fermentation broth is maintained at:

(a) a temperature between about 15° C. and about 100° C.;

(b) a pH between about 7.0 and about 13.9; and (c) for a time period between 0 and about 48 hours.

6. The process of claim 4, wherein during the step of pretreating the fermentation broth, the fermentation broth is maintained at:

(a) a temperature between about 55° C. and about 65° C.;

(b) a pH between about 9.0 and about 9.6; and (c) for a time period of about 2 hours.

7. The process of claim 4, further comprising the step of adjusting the pH of the fermentation broth using an inorganic base selected from the group consisting of ammonium hydroxide, NaOH, KOH, LiOH, and $Ca(OH)_2$.

8. The process of claim 1, wherein the extraction step comprises contacting the fermentation broth with a hydrophobic organic extraction solvent.

9. The process of claim 4, wherein the pre-treatment hydrophobic organic extraction solvent is selected from the group consisting of i-butyl acetate, n-butyl acetate, t-butyl acetate, ethyl acetate, propyl acetate, ethyl formate, butyl methyl ketone, dichloromethane, chloroform, carbon tetrachloride, dichloroethane, toluene, acetonitrile, methyl formate, methanol, ethanol, i-propanol, n-propanol, n-butanol, i-butanol, t-butanol, amyl alcohol and benzyl alcohol, and mixtures thereof.

10. The process of claim 8, wherein the hydrophobic organic extraction solvent is i-butyl acetate, n-butyl acetate, t-butyl acetate, ethyl acetate, propyl acetate, ethyl formate, butyl methyl ketone, dichloromethane, chloroform, carbon tetrachloride, dichloroethane, or toluene.

11. The process of claim 1, wherein the step of extracting the statin compound from the fermentation broth further comprises adjusting the pH of the fermentation broth to between about 1.0 and about 6.4.

12. The process of claim 11, wherein the pH of the fermentation broth is adjusted to between about 2.0 and about 4.5.

13. The process of claim 11, wherein the pH of the fermentation broth is adjusted with an acid selected from the group consisting of sulfuric acid and phosphoric acid.

14. The process of claim 1, wherein the step of extracting the statin compound from the fermentation broth further comprises adjusting the pH of the hydrophobic organic extraction solvent of step (b) to between about pH 1.0 and about 6.4.

15. The process of claim 1, wherein the hydrophobic organic extraction solvent of step (b) is selected from the group consisting of i-butyl acetate, n-butyl acetate t-butyl acetate, ethyl acetate, propyl acetate, ethyl formate, butyl methyl ketone, dichloromethane, chloroform, carbon tetrachloride, dichloroethane and toluene.

16. The process of claim 1, wherein following step (b), the hydrophobic organic extraction solvent is contacted with an aqueous solution containing a base.

17. The process of claim 16, wherein the base is selected from the group consisting of ammonium hydroxide, $NaHCO_3$ and $Na_2CO_3$.

18. The process of claim 1, wherein the hydrophobic organic extraction solvent is i-butyl acetate and the statin compound is compactin.

19. The process of claim 1, wherein the step of concentrating the solution of the hydrophobic organic extraction solvent containing the extracted statin compound is performed at reduced pressure.

20. The process of claim 1, wherein the step of concentrating the solution of the hydrophobic organic extraction solvent containing the extracted statin compound is performed by evaporation at a temperature below about 90° C.

21. The process of claim 1, wherein the step of crystallization is performed at temperature between about −10° C. and about 20° C.

22. The process of claim 21, wherein the step of crystallization is performed at temperature between about 0° C. and about 5° C.

23. The process of claim 21, wherein the step of crystallization is performed at temperature between about −10° C. and 0° C.

24. The process of claim 1, wherein the step of purifying the extracted statin compound by crystallization is performed using a solvent selected from the group consisting of ethanol, i-propanol, n-propanol, i-butanol, n-butanol, t-butanol, ethyl acetate, acetone, methanol, acetonitrile, ethyl formate, i-butyl acetate, t-butyl acetate, n-butyl acetate, toluene, propyl acetate, and butyl methyl ketone, and mixtures thereof.

25. A process for isolating a statin compound from a fermentation broth, wherein the statin compound comprises a carboxylic acid capable of forming a lactone and a fused bicyclic ring, the process comprising the steps of:

(a) pretreating the fermentation broth under alkaline condition to remove non-polar impurities;

(b) extracting the statin compound from the fermentation broth by contacting the fermentation broth with a hydrophobic organic extraction solvent, and extracting the statin compound from the fermentation broth into the hydrophobic solvent;

(c) separating the hydrophobic solvent from the fermentation broth;

(d) concentrating a solution of the hydrophobic solvent containing the extracted statin compound;

(e) washing the concentrated solution of the hydrophobic solvent with an aqueous solution containing base; and (f) purifying the extracted statin compound by crystallization.

26. The process of claim 25 wherein the aqueous basic solution comprises ammonium hydroxide, $NaHCO_3$ and $Na_2CO_3$.

27. The process of claim 25, wherein the statin compound is an inhibitor of HMG-CoA reductase.

28. The process of claim 1, wherein the purity of the isolated statin is greater than 99%.

29. The process of claim 25, wherein the purity of the isolated statin is greater than 99%.

* * * * *